United States Patent [19]

Miller

[11] Patent Number: 5,158,094
[45] Date of Patent: Oct. 27, 1992

[54] TURBINE INCENTIVE SPIROMETER

[75] Inventor: Kenneth G. Miller, Newport Beach, Calif.

[73] Assignee: Pegasus Research Corporation, Costa Mesa, Calif.

[21] Appl. No.: 598,532

[22] Filed: Oct. 16, 1990

[51] Int. Cl.[5] .............................................. A61B 5/00
[52] U.S. Cl. .................................... 128/726; 128/725; 73/861.88
[58] Field of Search ............... 128/726, 725, 720, 718; 73/861.79, 861.88

[56] References Cited

U.S. PATENT DOCUMENTS 4,572,209  2/1986  Boehringer .......................... 128/726

FOREIGN PATENT DOCUMENTS 1248226  8/1967  Fed. Rep. of Germany ...... 128/726
1096098  6/1955  France ................................ 128/726
0627359  6/1982  Switzerland ........................ 128/726

Primary Examiner—Francis Jaworski
Assistant Examiner—Scott R. Akers
Attorney, Agent, or Firm—Dressler, Goldsmith, Shore, Sutker & Milnamow, Ltd.

[57] ABSTRACT

An incentive spirometer that indicates the volume of air drawn therethrough is disclosed. The spirometer comprises a housing with a turbine rotatably mounted therein. The turbine is provided with a take-off shaft with which is operably associated a signal device responsive to the rotation of the shaft. Air drawn through the spirometer by a patient rotates the turbine and the signal device indicates the volume of air that has passed through the spirometer.

4 Claims, 3 Drawing Sheets

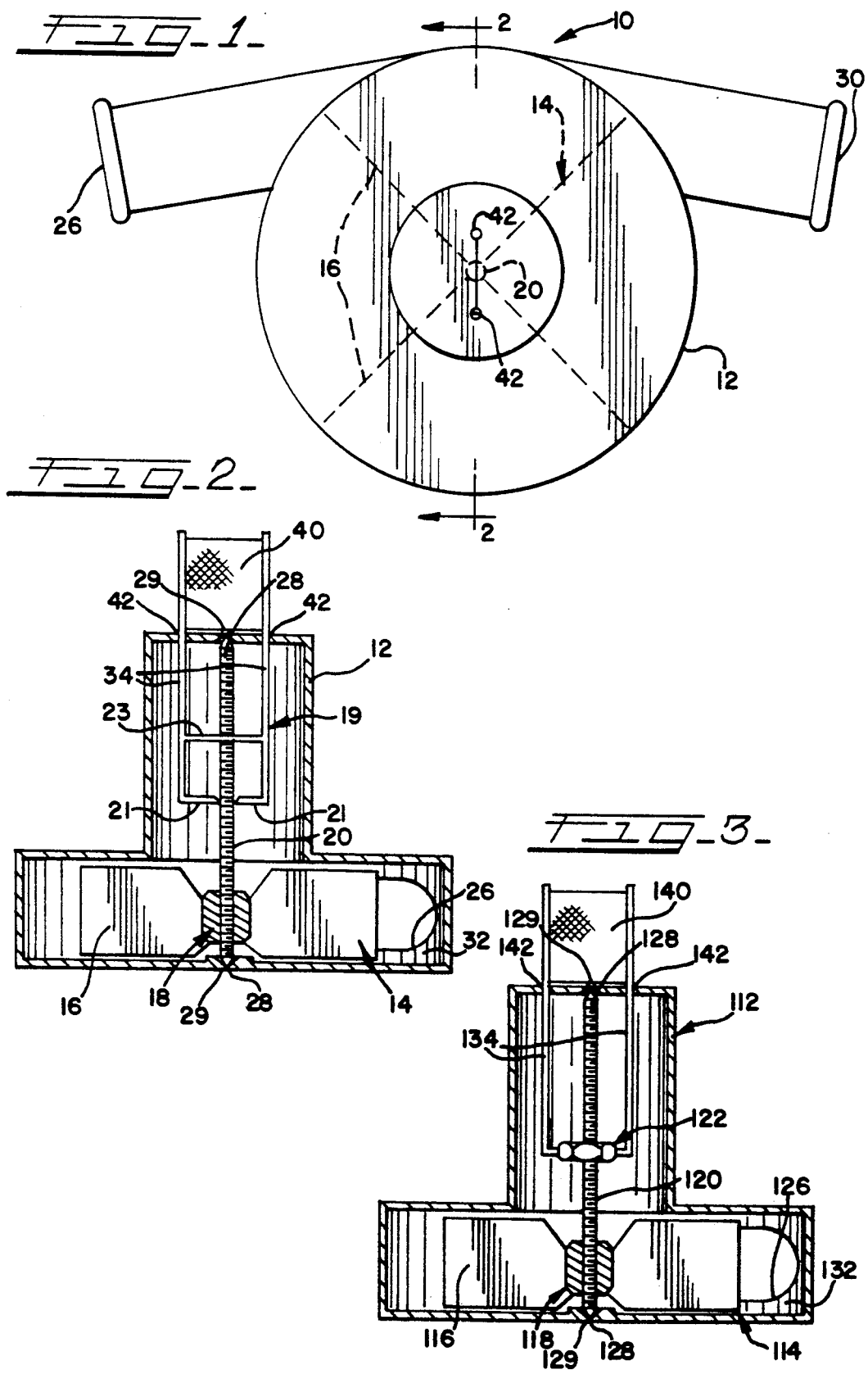

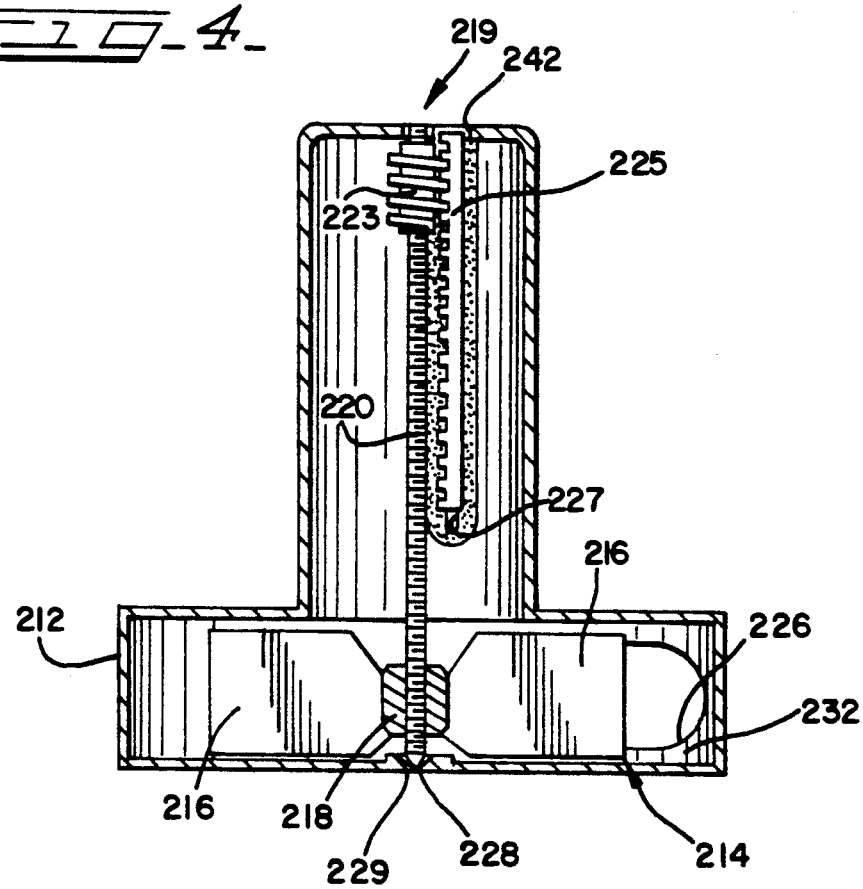
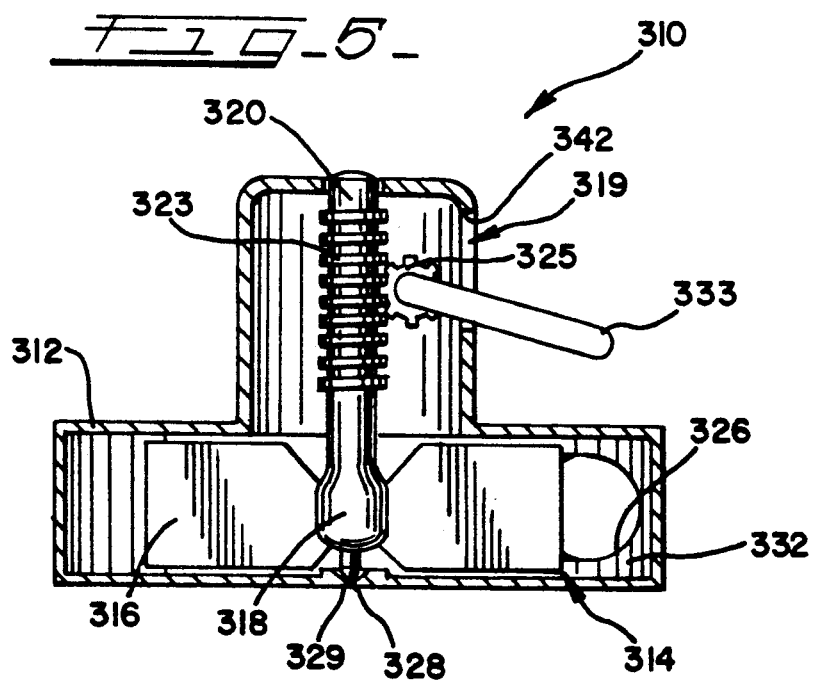

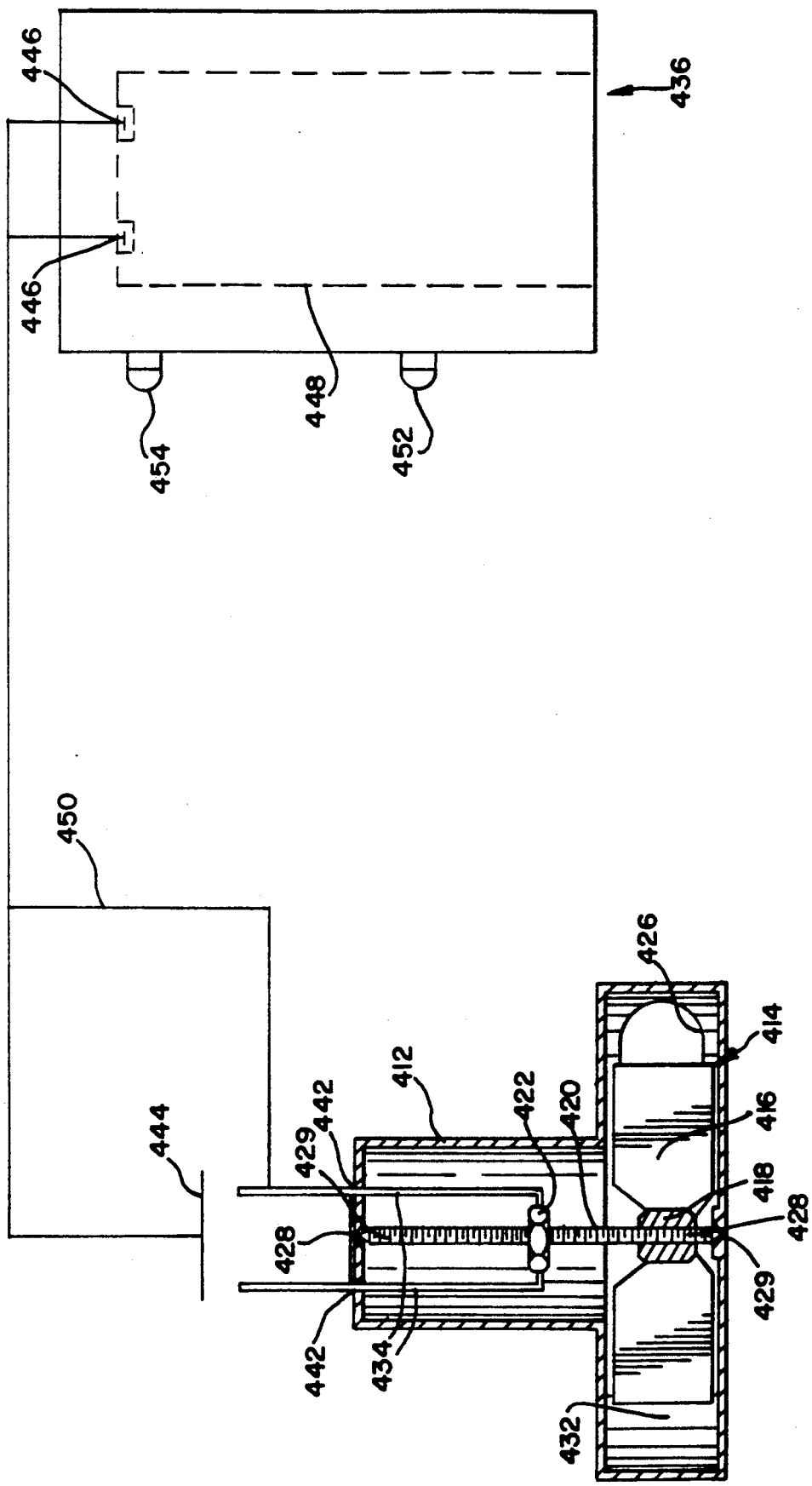

TURBINE INCENTIVE SPIROMETER

TECHNICAL FIELD

This invention relates to an incentive spirometer which indicates the volume of air that a patient draws or exhales. The spirometer includes a turbine which rotates as a patient draws air through the device and a signal means which reflects the turbine rotation, and thus the total volume of the air through the device.

BACKGROUND OF THE INVENTION

Incentive spirometers that communicate to patients the velocity or strength of a single breath are known in the art. Such incentive spirometers are used to train patients to breathe on their own after their breathing has been aided for a period of time by, for example, a respirator. However, prior art incentive spirometers do not necessarily help patients regain their lost lung capacity inasmuch as these spirometers do not enable patients to gauge their progress in this regard while breathing under their own power and according to their own capability.

Incentive spirometers heretofore known in the art have a traditional flow meter type of indicator in which a ball is suspended in a translucent or transparent column when air is being drawn through the spirometer. The position of the ball or similar object indicates that air is flowing through the spirometer. The closer the ball to the top of the column, the greater the velocity of the air being drawn through the column.

The flaw in the prior art spirometers is that they fail to indicate the volume of air being drawn by the patient into their lungs during a particular time period. Yet, the therapeutic value of the spirometer could be enhanced if a patient or therapist can gauge how much air is being drawn into the patient's lungs.

Also, the prior art spirometers do not provide the proper incentive, as they tend to make the patient want to breathe in a fashion that will draw the indicator up as high as possible in the gauge based on the velocity of the inhaled or exhaled air. When a patient with reduced lung capacity "fills" his or her lungs in this manner, a comparable amount of time and effort must be spent exhaling. This sporadic, deep breathing does not train the patient to breathe normally. As a result, though individual breaths may be taken at maximum flow indicated by the spirometers of the prior art, the total volume of air inhaled by the patient may not be increasing. Because the prior art spirometers do not indicate total volumetric flow, the patient or therapist may not necessarily realize that the patient's lung capacity is not improving during therapy.

Furthermore, prior art spirometers cannot be used to dispense medication because the total air flow cannot be measured. Most medication can only be administered in dosages that are measured by the volume of air administered with the dosage. Medication administered in too concentrated a dosage will be wasted and can have harmful effects as well. Medication administered in too low a dosage will be ineffective. Therefore, a spirometer that indicates the volume of air therethrough during any given time period is necessary to administer medication to a patient.

SUMMARY OF THE INVENTION

An incentive spirometer that indicates the volume of air drawn therethrough during a given time period is disclosed. This spirometer includes a turbine, rotatably mounted in a housing, which spins when air is drawn through the housing, and an indicator or signal mechanism operatively connected to the turbine to reflect the turbine revolutions and thus integrate the volume of air drawn through the device.

The rotatable turbine is journaled in the spirometer housing which also defines a fluid flow path such as a passage or channel through which air flows. The turbine has lightweight blades mounted to a rotatable take-off shaft. The passage or channel has an inlet and an outlet for the air drawn therethrough. The turbine blades are arranged to extend into the passage or channel. The passage and turbine are oriented to ensure that substantially all air flow through the channel moves the turbine blades.

The turbine is of relatively low weight and rotates freely in the housing. The rotating turbine has relatively little angular momentum and consequently, when the patient ceases to draw air through the apparatus, the turbine immediately ceases to rotate.

The signal mechanism that integrates the volume of air drawn through the turbine housing imparts negligible resistance to the rotation of the turbine. The signal mechanism includes a signal device driven by the rotation of the turbine take-off shaft. The shaft rotation is translated into axial movement of the signal device. The signal device preferably is a resettable travelling indicator equipped with flexible guides which engage threads on the take-off shaft and also move axially when the take-off shaft rotates. The guides are sufficiently rigid to enable the signal device to move axially as the take-off shaft, to which it is rotatably associated, rotates. Guides of rigid metal or plastic extend outwardly from the housing through openings provided therefor which prevent the rotation of the signal device with the shaft. These openings do not impede the axial movement of the guides.

The signal means can also utilize a rack-and-pinion arrangement to drive the signal device. The rack can extend outwardly through apertures in the housing that do not hinder or obstruct the axial movement of the rack. The rack is flexibly mounted in the housing, preferably so that the rack can be reset to its original starting position by exerting a small amount of pressure on the rack opposite its previous direction of travel or by temporarily spacing the rack from its cooperative pinion.

The movement of the signal device is proportional to the number of turbine rotations. Each rotation of the turbine represents a discrete volume of air that has been drawn through the spirometer and into the patient's lungs. The signal device can be calibrated, such as by providing suitable indicia associated with the guides, or the rack, to convert the rotation of the shaft into an indication of the volume of air that has been drawn through the turbine.

The housing may be transparent or translucent to permit the patient or therapist to observe the movement of the signal device in the housing.

Other features and advantages of the present invention will become readily apparent from the following detailed description, the accompanying drawings, and the appended claims.

BRIEF DESCRIPTION OF THE DRAWINGS

In the drawings, FIG. 1 is a diagrammatic plan view of a spirometer embodying the principles of the present invention;

FIG. 2 is a partial cross-sectional view of the incentive spirometer shown in FIG. 1 and taken along plane 2—2;

FIG. 3 is a partial cross-sectional view similar to that of FIG. 2 but showing an alternate signal means embodiment;

FIG. 4 is a partial cross-sectional view similar to that of FIG. 2 but showing a rack-and-pinion driven signal means;

FIG. 5 is a partial cross-sectional view similar to that of FIG. 2 but showing a circular rack-and-pinion driven indicator; and FIG. 6 is a view similar to FIG. 3 showing an alternative embodiment of the present invention including a battery energized volume indicator.

DETAILED DESCRIPTION OF THE PREFERRED EMBODIMENTS

While the present invention is susceptible of embodiment in various forms, presently preferred embodiments are shown in the drawings and will hereinafter be described with the understanding that the present disclosure is to be considered as an exemplification of the invention, but is not intended to limit the invention to the specific embodiments illustrated. For clarity, like parts with like functions in successive drawings have been given reference numbers having the same last two digits.

The incentive spirometer embodying this invention measures the volume of air that is drawn therethrough during a particular time period. Air drawn through this spirometer drives a turbine, the rotations of which are integrated to ascertain the volume of air flowing through the spirometer.

Referring to FIG. 1, incentive spirometer 10 has a housing 12 which encloses a rotatably mounted turbine 14 with blades 16 (shown in phantom) mounted on a take-off shaft 20. Housing 12 includes a generally cylindrical portion within which the turbine 14 is positioned. The housing further defines a substantially tangential air inlet 26 which communicates with an air outlet 30 through a passage 32 provided generally at the periphery of the cylindrical portion of housing 12.

When a patient draws a breath from air outlet 30, air is drawn from the atmosphere or other air source through inlet 26, into channel or passage 32, past turbine blades 16 and through outlet 30 to the patient. Passage 32 and housing 12 are constructed so that air, in order to pass through passage 32, must flow past the turbine blades 16. Thus, in order to flow from the inlet 26, through channel 32 to outlet 30, the air must "push" on at least one of the turbine blades 16 interposed in channel or passage 32 and thus rotate the turbine itself.

The freely spinning take-off shaft 20 (see FIG. 2) is threaded and rotates as the air drawn toward outlet 30 through passage 32 pushes the turbine blades 16. The turbine blades 16 are affixed to hub 18 which is attached to the shaft 20. The shaft continues to rotate as long as air is drawn through passage 32 that is part of the fluid flow path through the spirometer. When the air flow through passage 32 ceases, the take-off shaft 20 stops rotating.

The shaft 20 of turbine 14 is rotatably journaled in housing 12 by needle bearings 28 located at the upper and lower ends of shaft 20. The needle bearings 28 are received into and retained by journal-like retaining notches 29 in the housing 12. These needle bearings permit the shaft 20 to spin freely so that substantially no additional work is required for a patient to breathe through the apparatus than would be required if the patient were breathing freely without the apparatus. To further minimize the effort required to breathe through the apparatus, the turbine blades 16 are made of a lightweight plastic material such as polyvinyl acetate, nylon, celluloid, or the like, thereby minimizing the effort required to rotate the turbine 14.

Resettable indicator means 19 is mounted on take-off shaft 20 for movement along the longitudinal axis of shaft 20 and so that the shaft may rotate relative to the indicator means 19. The indicator means 19 is attached to shaft 20 by flexible pinchers 21 carried by guides 34 so that they engage the threads of the shaft 20. As the shaft 20 rotates, the pinchers 21 cause the resettable indicator means 19 to move axially along the shaft 20. The pinchers 21 usually are made of a polycarbonate web, or the like material, and are approximately 0.01 inches in thickness. This is sufficient to support the entire weight of the indicator means. The pincher web thickness may vary, however, depending upon the material of construction used as well as on the size of the threads on shaft 20. The pinchers 21 are sufficiently flexible, however, to enable the indicator means to be easily reset by exerting downward pressure on the indicator means 19. Slight pressure in the direction opposite of travel enables the indicator means 19 to be reset to its lowest point of travel on the shaft 20.

The guides 34 of indicator means 19 extend upwardly from pinchers 21 and through the housing 12 through openings 42 therein. The openings are slightly larger than the cross-sectional area of the guides 34 to permit free travel but not so large as to permit appreciable amounts of air to pass therethrough when the spirometer is in use. The guides 34 are free to move axially through openings 42 but are restrained from circumferential movement therein. An indicator card 40 is attached to the external portion of guides 34 and moves as the guides travel axially along the shaft 20. Displacement of the indicator card 40 indicates to the patient or therapist that a certain volume of air or a particular amount of medication, has been administered to the patient. The displacement of indicator card 40 can be suitably color-coded or calibrated as desired.

Indicator means 19 is also provided with a stabilizer bar 23 which connects the guides 34. A hole (not shown) is provided in stabilizer 23 which permits the shaft 20 to rotate freely without contacting the stabilizer bar.

FIG. 3 illustrates an alternate embodiment wherein a threaded follower 122 moves axially along shaft 120 as the shaft 120 rotates. The axial movement of the follower 122 indicates the volume of air that has passed through the spirometer. The follower 122 is also attached to off-center guides 134 which prevent the follower 122 from rotating with the shaft 120 as this shaft turns. As the shaft 120 rotates, follower 122 travels axially along the threaded portion of the shaft 120, also moving guides 134 axially along shaft 120. The friction forces resisting the rotation of shaft 120 in follower 122 are minimal. Frictional forces can be minimized by appropriate thread selection. For example, 6/32 inch threads, can be used for both the follower 122 and the shaft 120.

When the follower 122 engages either the housing 112 at the top of shaft 120 or the hub 118 near the bottom of shaft 120, its axial movement will cease and it must be reset. The axial movement of the follower 122 can be reversed by rotating the shaft 120 in the opposite direction, e.g., by reversing the air flow through the spirometer. The air flow can be reversed by having the patient take the next breath through inlet 126 by appropriate valving arrangement, in which event no resetting of the follower may be needed. The reversed air flow rotates the turbine 114 in the opposite direction during consecutive breaths in such a case.

In an alternate embodiment, when the follower 122 has travelled the entire length of the shaft 120, it can be reset to the opposite end of the shaft 120 by squeezing the off-center guides 134. The squeezing resiliently flexes the follower 122 to disengage the threads of the follower 122 from the threaded shaft 120. The patient or therapist can then slide the follower 122 to the opposite end of the shaft 120 as required.

In the embodiment illustrated in FIG. 4, turbine 214 is rotatably mounted in a fluid flow path defined by housing 212. Inlet aperture or port 226 is also defined by housing 212 and is shown behind the blades 216 of turbine 214. Shaft 220 passes through hub 218 and is journaled at the lower or proximal end by means of needle bearing 228 received in bearing seat 229. The upper portion of shaft 220 serves as a take-off shaft for the signal means 219.

In this particular embodiment the signal means 219 includes a rack-and-pinion assembly, more particularly a worm screw rack. Specifically, worm screw 223 is mounted to the distal end of shaft 220 and engages rack 225 slidably mounted for reciprocal movement along shaft 220 in channel or slot 227 formed in the sidewall of housing 212. As the worm screw 223 turns, driven by turbine 214, linear rack 225 extends through aperture 242 in the housing 212 and signals the volume of air that has passed through housing 212 driving turbine 214. Rack 225, or at least a face thereof, can be color coded to signal to the patient a desired target volume to be attained.

When the linear rack 225 reaches its maximum extension through aperture 229, the linear rack can be reset by disengaging the rack 227 from the worm screw 223, exerting force on the rack 225 in the opposite direction of travel and re-engaging the worm screw 223 with the rack 225. In a preferred embodiment, deformation of the flexible housing 212 will disengage the worm screw 223 from the rack 225.

The embodiment shown in FIG. 5 illustrates yet another rack-and-pinion assembly for the signal means 319 of the present incentive spirometer. In this particular instance a circular rack-and-pinion arrangement is utilized. Specifically, pinion 322 cooperates with circular rack 325 to elevate an elongated member such as a signal flag or lever 333 as turbine 314 and thus shaft 320 rotates.

The circular rack 325 is pivotally mounted onto the housing 312. An aperture 342 is provided in the housing 312 through which the flag or lever 333 extends. The arcuate movement of the portion of the lever 333 that extends through the housing indicates the volume of air that has passed through the turbine 314. The travel of the lever 333 is limited by the size of the aperture 342.

When the lever 333 encounters the housing 312, the signal means 319 must be reset. The signal means 319 can be reset by disengaging the pinion 323 from the rack 325 and moving the lever 333 to its starting position. The pinion 323 can be disengaged from the rack 325 by pulling lever 333 away from the rack 325. In a preferred embodiment, the housing 312 is sufficiently flexible so that a moderate pulling force on lever 333 will disengage the pinion 323 from the rack 325, yet resilient enough for the pinion 323 to re-engage the rack 325 when the pulling force ceases.

Optionally, if the guides 434 are metal or equipped with metallic contact surfaces, they can be connected to an electronic indicator 436 as depicted diagrammatically in FIG. 6 to provide a signal that is perceivable by patient's sensory perception, e.g., audibly, visually or by tactile means. A circuit is completed when the follower 422 has travelled a preset distance along the shaft 420 and the metal guides 434 are brought into contact with the electrical contact 444. Both electrical contact 444 and metal guides 434 are connected via electrical wire 50 to the terminals 446 of a power source 448. In a preferred embodiment, power source 448 is a battery. When metal guides 434 come into contact with electrical contact 444, an indicator light or buzzer 452 indicates that the volumetric goal has been achieved. In an alternate embodiment, a second indicator light or buzzer 454 is illuminated when the electrical contact 444 and the guides 434 are not in contact. The second indicator light or buzzer 454 may also be associated with a counter to indicate the number of times the patient's volumetric goal has been achieved.

In yet another embodiment, the indicator 452 is a digital indicator which communicates to the patient or therapist the actual volume of air inhaled by the patient in a single cycle. The instrument is calibrated so that travel of the follower along the shaft 420 is converted to a reading that corresponds to the volume of air that flows through the spirometer 410. The instrument can thus indicate the volume of air that flows through the apparatus by sensing the movement of the indicator means 419 on shaft 420.

The following illustrations were intended by way of example only to highlight the concepts embodied by the invention. They are not intended to limit the invention in any manner. Modifications and variants of these examples are within the spirit and scope of this invention and are included within the appended claims as those in the art would readily appreciate.

I claim:

1. An incentive spirometer suitable for indicating the volume of air to a patient which spirometer comprises:
 a housing defining an inlet and an outlet for the housing and a passage that provides a fluid flow path between the inlet and the outlet;
 a rotatable turbine mounted in the housing and situated in said fluid flow path; and
 a signal means operatively connected to said turbine integrating the volume of air that has passed through the housing and comprising a rotatable shaft connected to said turbine, a shaft follower which moves axially along the shaft while the shaft is rotating, and a flag device attached to said shaft follower; said shaft follower being a pincher means releasably associated with the shaft and moving axially along the shaft while the shaft is rotating.

2. The spirometer of claim 1 wherein the pincher means are flexible and resilient, enabling the shaft follower to be moved manually by force exerted in the direction opposite the axial movement of the indicator means.

3. The spirometer of claim 1 wherein the flag device restrains the shaft follower from circumferential rotation with the shaft, and comprises at least one rigid member which extends outward from the housing through an opening in the housing provided therefor.

4. The spirometer of claim 3 wherein the portion of the flag device extending outward from the housing is attached to a gauge which indicates the volume of air that has passed through the turbine by the axial movement of the shaft follower and the signal device attached thereto.

* * * * *